United States Patent
Bologovsky et al.

[11] Patent Number: 5,950,627
[45] Date of Patent: Sep. 14, 1999

[54] SPINE BOARD

[75] Inventors: Michael Thomas Bologovsky, Millbrook; John Cline, Union Vale; Russell Ralph Mohberg, Mount Kisco; Richard Sunderland, Hopewell Junction, all of N.Y.

[73] Assignee: Laerdal Medical Corporation, Wappinger Falls, N.Y.

[21] Appl. No.: 08/773,045

[22] Filed: Dec. 24, 1996

[51] Int. Cl.[6] ..................................... A61B 19/00
[52] U.S. Cl. ............................. 128/869; 128/870; 5/82 R
[58] Field of Search ................................... 128/845, 846, 128/869, 870; 5/624–636

[56] References Cited

U.S. PATENT DOCUMENTS

D. 328,351   7/1992   Ott .
D. 329,216   9/1992   Beeley et al. .

(List continued on next page.)

FOREIGN PATENT DOCUMENTS

| 0 023 115 | 1/1981 | European Pat. Off. . |
| 0 123 474 | 9/1984 | European Pat. Off. . |
| 0 252 672 | 1/1988 | European Pat. Off. . |
| 0 416 664 | 3/1991 | European Pat. Off. . |
| WO 94/08542 | 4/1994 | WIPO . |
| WO 94/13240 | 6/1994 | WIPO . |

OTHER PUBLICATIONS

Spine–X Literature, Design Principles, Inc., 1 p.
Life + Lite Literature, Design Principles, Inc., 1 p.
Headbed II Literature, Laerdal, 2 pp.
NAJO Emergency Product Literature, 2 pp.
Rediboard Literature, NAJO, 2 pp.
Identifier Spineboards Literature, 1 p.
Bak–Pak Product Literature, RAO Medical Device, 1995, 1 p.
Stabilizer, *Moore Medical Catalog*, "Winter 1996", p. 18.
Bak–Pak Advertising Literature, 1 p.
Bak–Pak Advertising Literature, 1 p.
Bak–Pak Advertising Literature, 1 p.
Bak–Pak Advertising Literature, 1 p.
Bak–Pak Order Sheet, 1 p.
Bak–Pak Order Sheet, 1 p.
Moore Safety Immobilization Strap Advertisement, Moore Medical Corp., (8), 1 p.
HDx Backboard™, *Moore Medical Catalog 1034*, 1996, p. 39.
Identifier Spineboards, *Moore Medical Catalog 1034*, 1996, p. 38.
Dolphin Spine Board, *Moore Medical Catalog 1034*, 1996, p. 37.
Hare® Wooden Spine Boards with Melamine, *Moore Medical Catalog 1034*, 1996, p. 33.
Dyna–Lite™ Spine Boards, *Moore Medical Catalog 1034*, 1996, p. 35.
Short Spine Board Sets, *Moore Medical Catalog 1034*, 1996, p. 31.
Hare® Short Wooden Spine Boards, *Moore Medical Catalog 1034*, 1996, p. 30.
Hare® Long Wooden Spine Boards, *Moore Medical Catalog 1034*, 1996, p. 32.
Bak–Pak Spine Board, *Moore Medical Catalog 1034*, 1996, p. 36.
Iron Duck Ultraloc Immobilization System, *Moore Medical Catalog 1034*, 1996, p. 34.

*Primary Examiner*—Michael A. Brown
*Attorney, Agent, or Firm*—Kenyon & Kenyon

[57] ABSTRACT

A spine board having internal stiffening elements mechanically connected to an outer shell via a number of speed pins. A quantity of urethane foam fills the spaces between the stiffening elements and the shell. The speed pins permit the rotational molding of the shell about a pair of graphite reinforcing tubes, which better distributes the loads to be born among the outer shell, urethane filler, and stiffening elements, thereby increasing the life span of the board.

60 Claims, 6 Drawing Sheets

U.S. PATENT DOCUMENTS

| | | |
|---|---|---|
| D. 338,177 | 8/1993 | Kimball . |
| D. 353,203 | 12/1994 | LeCompte . |
| D. 358,652 | 5/1995 | Pretzer . |
| 2,141,100 | 12/1938 | Warden . |
| 3,469,268 | 9/1969 | Phillips . |
| 3,707,734 | 1/1973 | Matthews . |
| 3,737,923 | 6/1973 | Prolo . |
| 4,017,234 | 4/1977 | Andrews et al. . |
| 4,064,574 | 12/1977 | Schnitzler . |
| 4,067,079 | 1/1978 | Buchman . |
| 4,141,368 | 2/1979 | Meyer . |
| 4,143,654 | 3/1979 | Sherman . |
| 4,188,428 | 2/1980 | Wolf . |
| 4,220,147 | 9/1980 | Allen, III . |
| 4,226,231 | 10/1980 | Andersen . |
| 4,261,349 | 4/1981 | Lambson et al. . |
| 4,267,830 | 5/1981 | Vick . |
| 4,280,490 | 7/1981 | Santy . |
| 4,299,210 | 11/1981 | Santy . |
| 4,369,982 | 1/1983 | Hein et al. . |
| 4,473,912 | 10/1984 | Scheidel et al. . |
| 4,506,664 | 3/1985 | Brault . |
| 4,519,106 | 5/1985 | Sandquist . |
| 4,528,981 | 7/1985 | Behar . |
| 4,594,999 | 6/1986 | Nesbitt . |
| 4,612,678 | 9/1986 | Fitsch . |
| 4,640,275 | 2/1987 | Buzzese et al. . |
| 4,655,206 | 4/1987 | Moody . |
| 4,699,152 | 10/1987 | Carville . |
| 4,710,991 | 12/1987 | Wilmore et al. . |
| 4,718,412 | 1/1988 | Nesbitt . |
| 4,736,474 | 4/1988 | Moran et al. . |
| 4,794,656 | 1/1989 | Henley, Jr. . |
| 4,841,961 | 6/1989 | Burlage et al. . |
| 4,854,305 | 8/1989 | Bremer . |
| 4,895,173 | 1/1990 | Brault et al. . |
| 4,899,736 | 2/1990 | Nesbitt . |
| 4,905,712 | 3/1990 | Bowlin et al. ............ 128/870 |
| 4,928,711 | 5/1990 | Williams . |
| 4,936,296 | 6/1990 | Russel . |
| 4,943,223 | 7/1990 | Panaromi . |
| 4,979,520 | 12/1990 | Boone, Jr. et al. . |
| 4,993,092 | 2/1991 | Weeks . |
| 4,994,132 | 2/1991 | Lickens et al. . |
| 5,014,374 | 5/1991 | Williams . |
| 5,022,838 | 6/1991 | Payne . |
| 5,048,134 | 9/1991 | Dennill et al. . |
| 5,048,541 | 9/1991 | Haneline . |
| 5,058,575 | 10/1991 | Anderson . |
| 5,083,574 | 1/1992 | Schlutow . |
| 5,088,137 | 2/1992 | Rose . |
| 5,094,608 | 3/1992 | Piazza et al. . |
| 5,113,876 | 5/1992 | Herman . |
| 5,118,555 | 6/1992 | Horovitz . |
| 5,148,815 | 9/1992 | Britton . |
| 5,154,186 | 10/1992 | Laurin et al. . |
| 5,188,845 | 2/1993 | Payne . |
| 5,211,185 | 5/1993 | Garth et al. . |
| 5,211,186 | 5/1993 | Shoemaker et al. . |
| 5,243,639 | 9/1993 | Johnson . |
| 5,255,303 | 10/1993 | DiMaio et al. . |
| 5,263,214 | 11/1993 | McLaughlin et al. . |
| 5,274,864 | 1/1994 | Morgan . |
| 5,285,797 | 2/1994 | Zeller . |
| 5,306,026 | 4/1994 | Jesse . |
| 5,316,701 | 5/1994 | Payne . |
| 5,318,734 | 6/1994 | Palmersten et al. . |
| 5,334,133 | 8/1994 | Carroll . |
| 5,360,393 | 11/1994 | Garth et al. . |
| 5,414,883 | 5/1995 | Fangrow, Jr. ............ 128/870 |
| 5,422,928 | 6/1995 | Payne . |
| 5,435,323 | 7/1995 | Rudy ............ 128/870 |
| 5,445,403 | 8/1995 | Cazaillon et al. . |
| 5,472,004 | 12/1995 | Gilliard . |
| 5,473,784 | 12/1995 | Nixon et al. . |
| 5,507,632 | 4/1996 | Payne . |
| 5,509,710 | 4/1996 | Eavenson, Sr. et al. . |
| 5,515,869 | 5/1996 | Powell et al. . |
| 5,518,806 | 5/1996 | Eder et al. . |
| 5,547,725 | 8/1996 | Barrows et al. . |
| 5,560,054 | 10/1996 | McQueen ............ 128/870 |

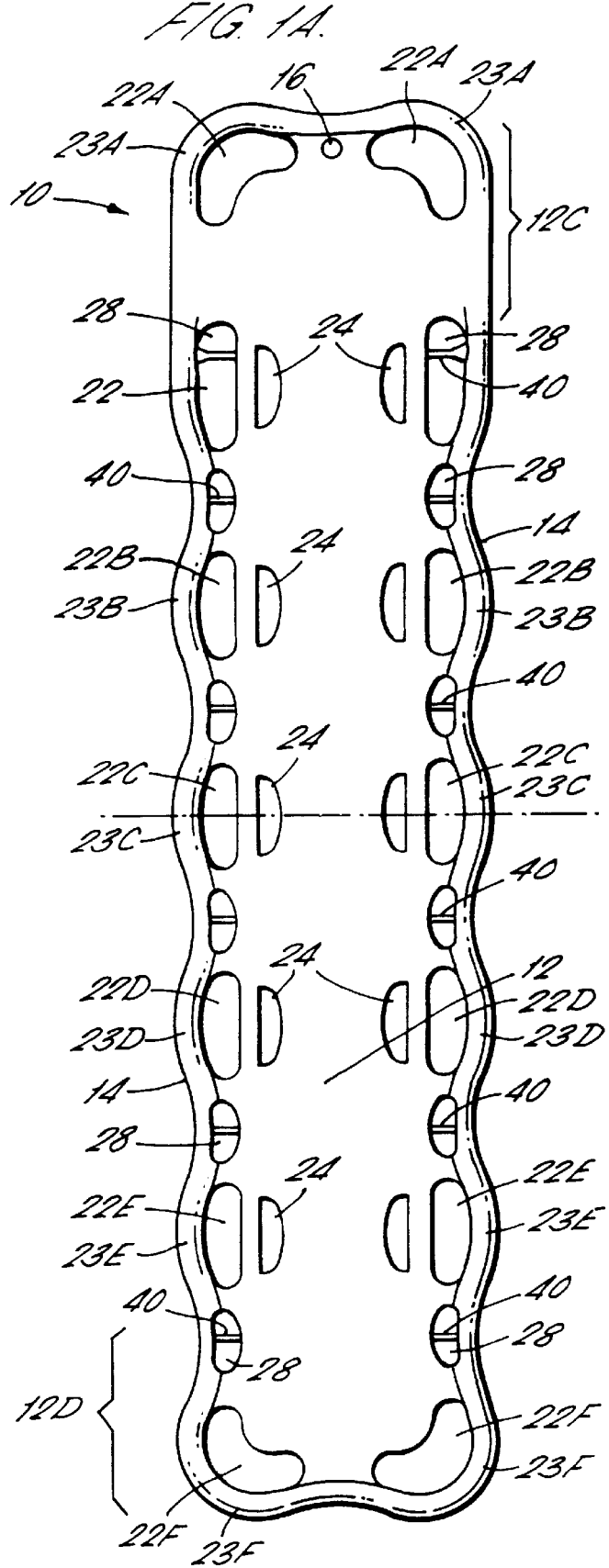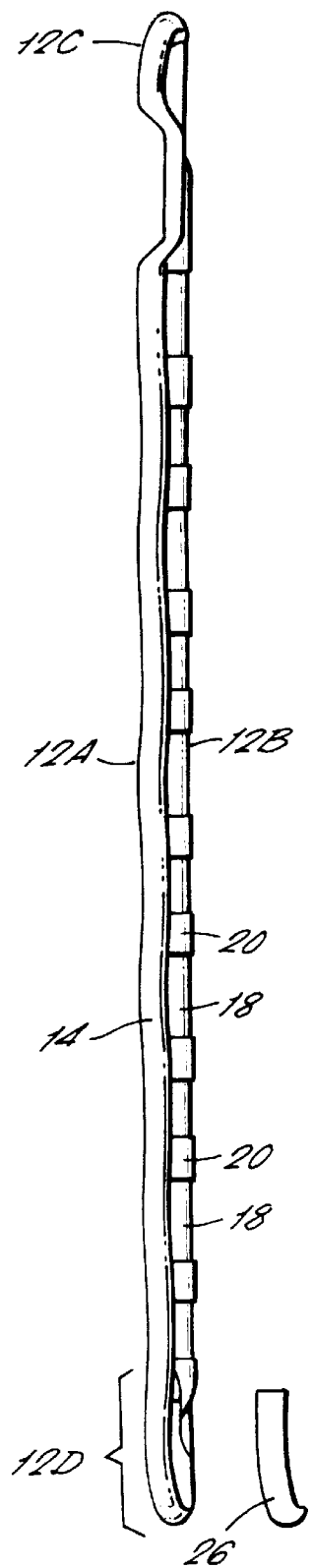

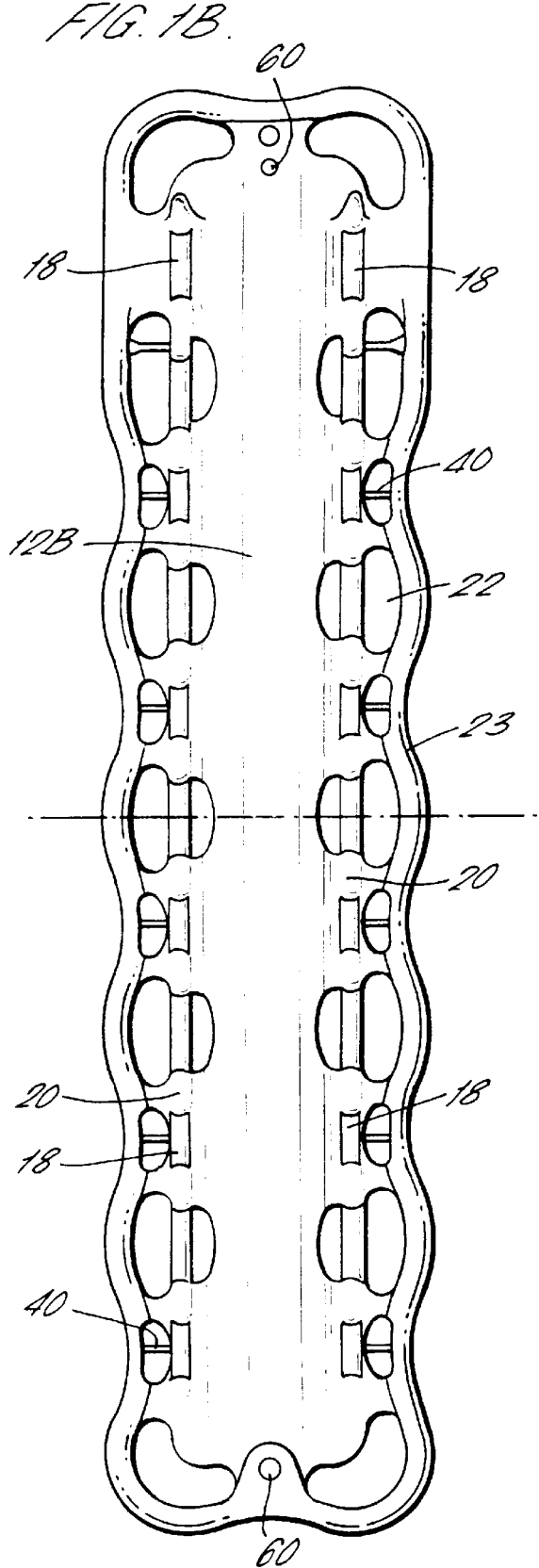

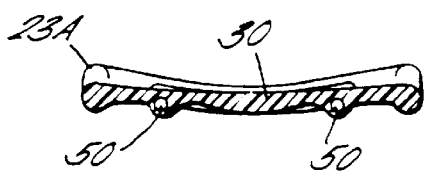
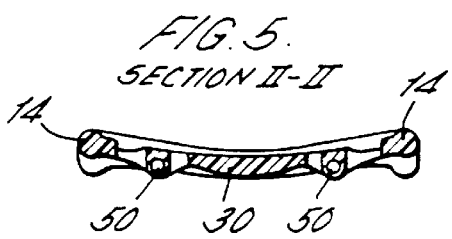
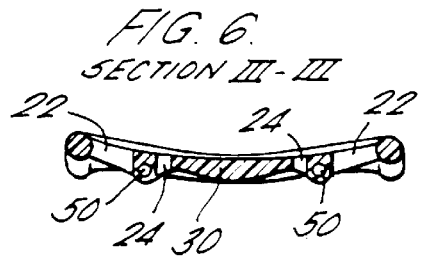
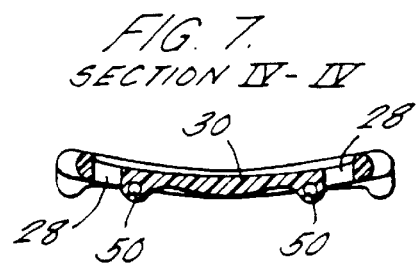
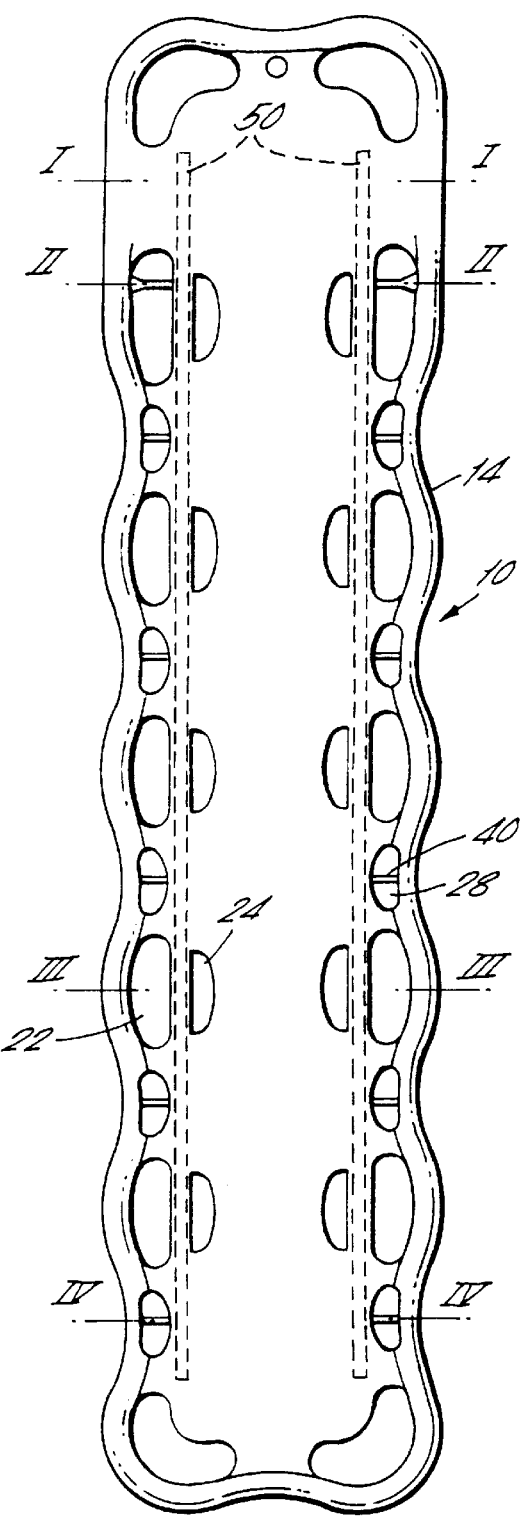

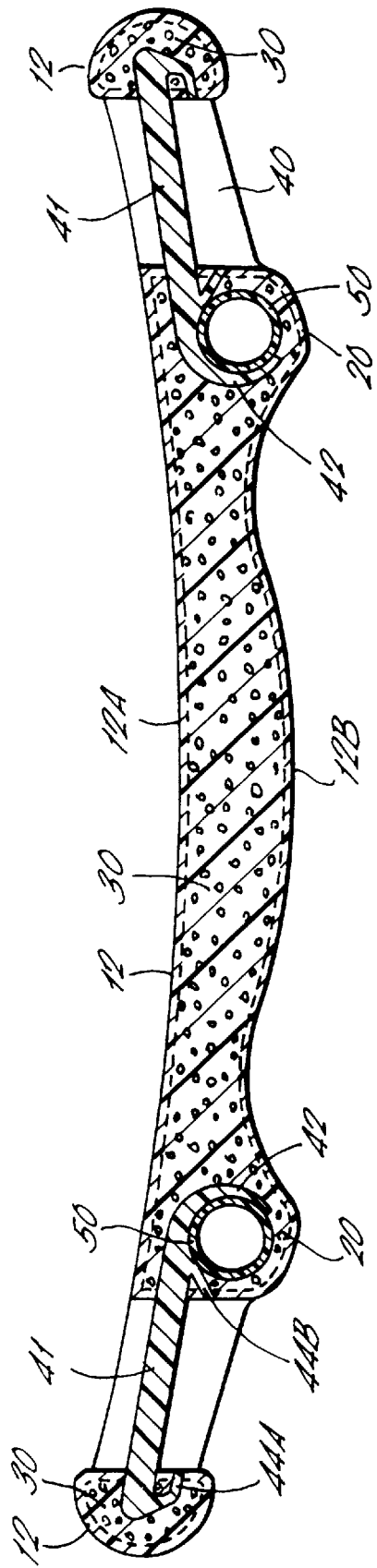

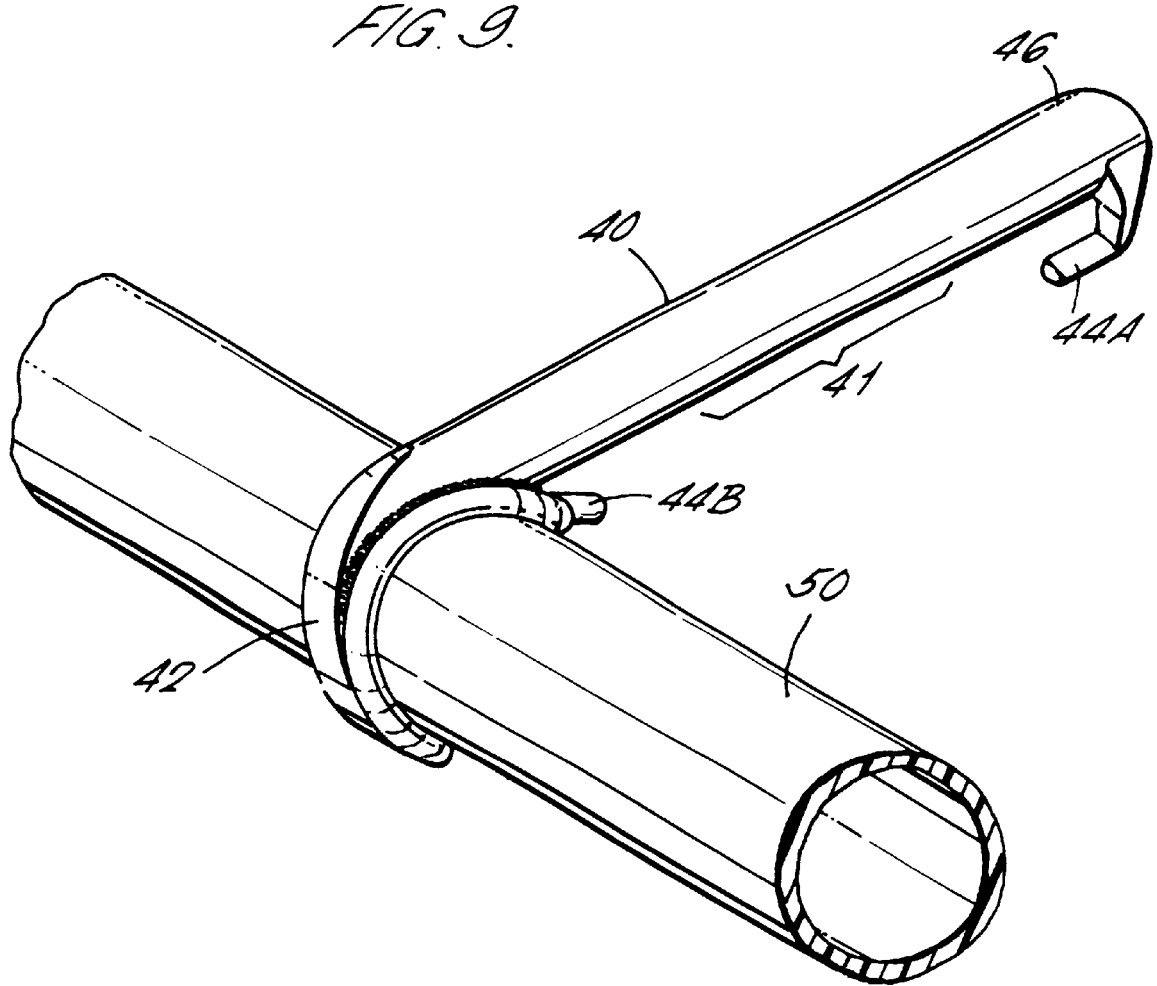

SPINE BOARD

FIELD OF THE INVENTION

The present invention relates generally to an improved spine board of the type employed by paramedics for transporting injured individuals.

BACKGROUND OF THE INVENTION

Spine boards have been used by physicians and emergency medical technicians for a number of years in the transport of injured or incapacitated individuals. In general terms, spine boards typically are rectangular boards on which the injured individual is placed. A strapping system is used to secure the individual to the board. The primary purpose of the spine board is to enable the transport of an injured person without injury to his spinal column. The great utility of the spine board has led to it becoming one of the standard pieces of equipment typically found in an ambulance (where the scarcity of space permits only the most useful pieces of equipment).

A principal functional requirement of a spine board is that it enable the transport of an injured person without injury to his spinal column. Therefore, the spinal board must be rigid, even when used to transport heavy patients, for excessive flexion of the spine board can exacerbate spinal injuries. On the other hand, it is desirable that such boards be as light as possible, since they often must be carried in unpredictable and challenging settings.

One approach to meeting these basic design criteria has been to use internal stiffening elements to impart extra rigidity to the spine board. For example, one commercially available spine board employs a plastic outer shell that is filled with foam. Suspended within the foam are reinforcing rods to impart some greater stiffness to the board. These rods are free-floating within the foam, in that they are inserted into the spine board after formation of the shell and prior to addition of foam. During use, this (and similar) spine boards is subjected to irregular cyclical loading as patients of varying shape and weight are placed on, carried, and removed from the spine board. These loading patterns can cause the foam adjacent the stiffening rods to compress with time, thereby creating voids in which the stiffening elements are not properly supported. This in turn, leads to further compression and deformation of the foam during loading, which further compromises the structural integrity of the board.

Hence, there is a need for a spine board that is as rigid after many cyclic loadings as it is when first loaded with a patient, yet which also is lightweight.

Other deficiencies that other approaches have presented lie in the placement of stiffening elements within the central portion of the board. This can be troublesome since patients may have to be x-rayed while still on the board, and materials that are suitable for use as stiffening elements generally block x-rays. Hence, the presence of stiffening elements within the x-ray field of interest may occlude the desired field of interest.

In use, the patient is secured to the spine board with strapping. The manner in which an injured individual is strapped to a spine board may vary, depending on such divergent factors as the condition of the individual, the preferences of the supplier of the board, and the economics of various strapping approaches. There are many different types of strapping systems available. Unfortunately, some spine boards offer only "closed architecture" strapping systems, in that the board can not readily be modified to accept other strapping systems. There is a further need for a spine board that permits the use of a broad array of strapping elements. consideration in the use of spine boards is the risk presented by microbial contamination. Injured individuals who are transported on spine boards are often both the source and recipient of significant microbial cross contamination (as through open wounds). Such cross contamination may be patient to patient as noted, or patient to care provider. There is a need for a spine board that is resistant to microbial growths and that is easy to disinfect.

SUMMARY AND OBJECTS OF THE INVENTION

It is an object of this invention to provide a spine board that is rigid.

It is an object of this invention to provide a spine board that is light weight.

It is an object of this invention to provide a spine board that is both light weight and sufficiently rigid to transport patients.

It is an object of this invention to provide a spine board that is long-lasting in use.

It is an object of this invention to provide a spine board that can be used with x-ray apparatus.

It is an object of this invention to provide a spine board that permits the use of a wide array of strapping schemes.

It is an object of this invention to provide a spine board that is resistant to microbial growth.

These and other objects are met with a spine board having a rotationally molded outer polymer shell that contains both filler and discrete stiffening elements. The spine board of the present invention thus has both inner and outer structural elements, linked in a structurally integrated manner during the molding process.

Located within the spine board and in close proximity to its outer shell are two carbon graphite tubes that act as stiffening elements, running approximately the length of the spine board. The materials of the spine board are X-ray transparent, with the exception of the high proton density stiffening elements. Therefore, in order to provide an x-ray field likely to permit visualization of most patients, the stiffening components are widely spaced apart. Mounted on each of the tubes are a series of location pins commonly referred to as speed pins, which are plastic elements that can be clipped or slidably mounted onto the tubes with sufficient force so as to permit the suspension of the tubes in a mold cavity. The location of the speed pins is determined both by mechanical considerations and in consideration of the locations at which the user of the board may wish to attach strapping.

Each of the speed pins has two ends, one of which is connected to one of the reinforcing tube and the other of which is connected to a rotationally molded shell made of high density polyethylene or other suitable material. The speed pins and reinforcing tubes are inserted into a rotational mold prior to the formation of the shell, so that they are inserted-molded in place.

A quantity of catalyzed urethane foam fills the spaces between the outer shell, speed pins, and tubes (except for spaces for hand-holds and areas where the speed pins are exposed to accept strapping).

The spine board affords two built-in forms of prophylaxis against microbes. First, as the material of the shell cools and solidifies, it contracts about the speed pins, preventing the formation of open pockets where bacteria can become established. Second, the material of the shell, speed pins and strapping may optionally be provided with a quantity of antimicrobial agent, added to the polymer mix prior to molding.

The spine board of this design thus links the outer shell, speed pins, and reinforcing tubes in a tightly integrated package that affords great stiffness with little weight penalty, and also is inherently resistant to microbial in-growths. By insert molding the reinforcing elements into the interior of the outer shell prior to the introduction of the urethane filler, one obtains a better distribution of the loading forces encountered during use, and thus a product that offers greater longevity.

BRIEF DESCRIPTION OF THE FIGURES

For a more complete understanding of this invention, reference should now be made to the exemplary embodiment illustrated in greater detail in the accompanying drawings and described below. In the drawings:

FIG. 1A. Is a top plan view of a spine board constructed according to the principles of the invention;

FIG. 1B. Is a bottom plan view of a spine board constructed according to the principles of the invention;

FIG. 2. Is a side-elevational view of the spine board of FIG. 1;

FIG. 3. Is a view of the spine board similar to that presented in FIG. 1, but further showing, in phantom, carbon fiber reinforcing tubes.

FIGS. 4–7 are sectional views of the spine board of FIG. 3, taken along sections I—I, II—II, III—III, and IV—IV respectively, in which the speed pins are not shown.

FIG. 8 is a sectional view of the spine board taken along line IV—IV of FIG. 3, further showing the use of speed pins and differentiating between the outer shell and urethane core of the spine board.

FIG. 9 is a perspective view of the speed pin and its connection to the graphite reinforcing tube.

DETAILED DESCRIPTION

Figure 10:
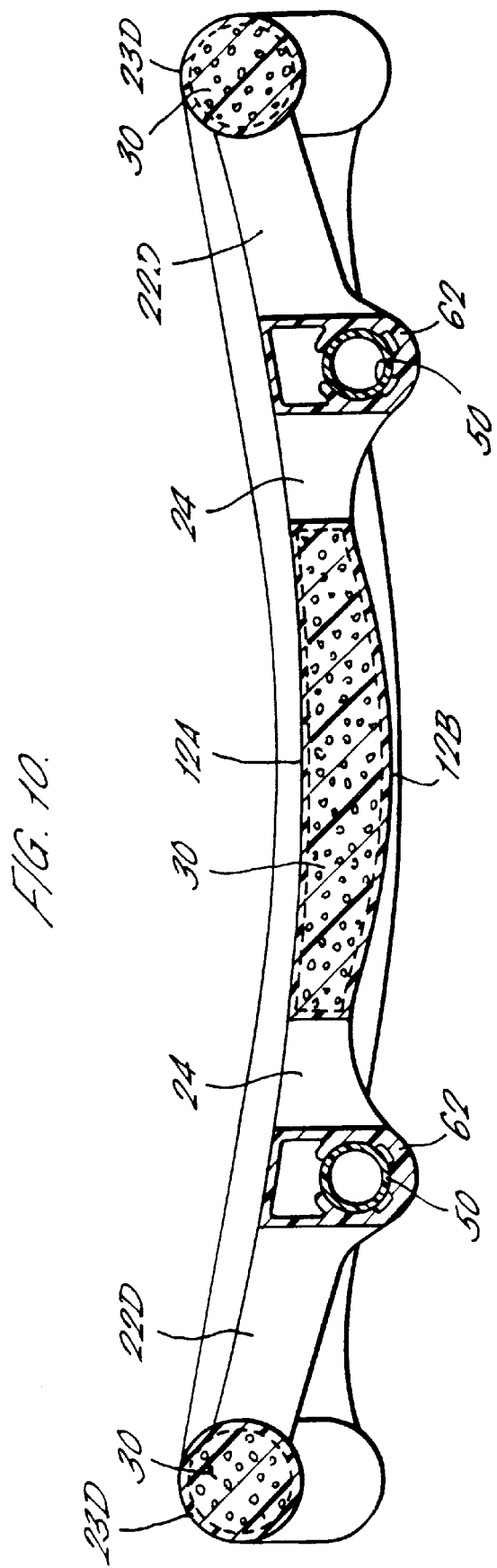
FIG. 10 is a sectional view of an embodiment of the spine board, taken along line III—III of FIG. 1, in which the reinforcing tubes are mechanically linked to the outer shell by webbing.

Referring now to the drawings, wherein like numerals indicate like parts throughout, the principal components of a preferred embodiment of a spine board 10 are illustrated in FIGS. 1–3. The spine board comprises an outer shell 12, a pair of reinforcing tubes 50 (shown in phantom in FIG. 3), and a series of speed pins 40 that link the reinforcing tubes 50 to the shell 12. The space between the outer shell and the reinforcing tubes and speed pins is filled with a foam material 30 of uniform distribution and density.

The shell 12 has an upper surface 12a for bearing a patient, an underside 12b that can be placed to rest either on ground or on a gurney, a head portion 12c and a foot portion 12d. The head portion 12c is provided with an attachment means (such as a hole 16) for facilitating attachment of certain cervical immobilization devices. Such devices are often used with spine boards to help prevent injury to the spinal column, particularly the cervical region or neck, during patient transfer to a medical facility. For example, the cervical region of the patient's spine (which is especially vulnerable) is typically secured and immobilized using a cervical collar, such as that disclosed in U.S. Reissue Pat. No. 32,219 to Garth.

Other head and neck securing devices can be used with this spine board in addition to or in place of a cervical collar. These vary in design, and the instant spine board 10 is designed to accommodate these. One example of an immobilization device that can be used with this board in conjunction with a cervical collar is set forth in U.S. Pat. No. 5,360,393 to Garth et al. This patent discloses a disposable cardboard, plastic film and adhesive system which attaches to spine boards by means of an adhesive-backed tape. This device is used to minimize rotational movement of the patient's spinal column during patient transportation.

The underside 12B of the spine board outer shell 12 is provided with a series of ground contact sections 20 (see FIG. 2) on which the spine board can rest when placed on the ground. These contact points 20 are formed in the outer shell about the reinforcing tubes 50 (which are further discussed below).

The peripheral portions of the spine board 10 are provided with a series of hand holes 22A–F and lifting handles 23A–F, spaced along the perimeter of the spine board. The spine board 10 can be hand-carried by two or more paramedics lifting the spine board 10 by these handles 23. Generally speaking, at least two individuals are employed to effectively carry a patient strapped to the spine board 10. However, the spine board can, under certain circumstances, be dragged by a single paramedic. If necessary, a lone paramedic can lift the spine board 10 via the handles 23A located at the head of the board, and drag it along the ground on detachable wear skids 26 optionally located at the underside of the foot region 12d or head region 12c to protect the spine board from abrasion. Of course, the spine board 10 can be dragged along its other end as well.

The patient will generally be secured to the spine board by means of straps crossing the patient's abdomen, extremities (legs and feet), and thoracic region. Such straps are typically adjustable in order that the required degree of tightness may be achieved as is dictated by the patient's condition. Certain trauma conditions may dictate varying degrees of unrestricted access to the patient. As noted, such strapping may be provided in a number of ways. Therefore, the spine board is designed to allow as much flexibility in selection of strapping as is reasonably possible without compromising the structural and mechanical aspects of the product's design. The spine board 10 provides an open architecture with respect to the strapping it will accommodate, in that it can accommodate a wide array of straps and strapping systems.

For example, the periphery 14 of the spine board 10 is curvilinear or undulating, so as to allow the use of certain "Wrap-Around" techniques of patient securement. "Wrap-Around" describes the application of a single strap to the spine board 10. The undulating edges 14 of the spine board 10 cause the straps to tighten as the patient shifts, thereby preventing the patient from slipping longitudinally on the spine board 10. In certain circumstances, as when a patient must be moved with his head elevated above the level of his feet (this can occur when he is being moved down a staircase), such securement is particularly useful in preventing longitudinal slippage of the strapping. This feature is of particular importance to air lift paramedics.

In addition to the use of the single-strap wrap around method, multiple straps may be employed. These are attached to the spine board 10 via standard clips hooked to one or more of the speed pins 40 located in the speed pin holes 28 on the lateral sides of the board. The straps employed may be disposable or non-disposable, and can vary in length or width, as well as in the particular hardware by which they are attached to the spine board. (Examples of strapping approaches are set forth in U.S. Pat. No. 5,211,186 to Shoemaker et al. and U.S. Pat. No. 4,794,656 to Henley, the contents of which are incorporated herein for this purpose.)

The speed pins 40, hand holes 22, and periphery of the board afford a wide array of strapping options for most patients. However, some patients may be of such small stature (e.g., children) that it may be desirable to provide a narrower wrap than the outer periphery of the board can provide. To that end, more medially located pediatric strapping slots are provided to facilitate the immobilization of children, for whom the outer strapping areas may be too far apart for proper securement.

A series of flattened recessed areas 19 is located an the underside 12B of the outer shell (see FIG. 1B), intermediate the hand holes 22 and pediatric holes 24. These recesses 19 help guide the placement of the straps about the board.

One of the fundamental design considerations of a spine board is that it be rigid, particularly in the sense of resisting flexion about its midline axis (see FIG. 1), where bending under the weight of a patient is most likely to arise. On the other hand, it is desirable to make the spine board as light as possible, so as to facilitate its use in what are often hazardous and unpredictable circumstances. Prior approaches to these design considerations have often led to one consideration being permitted to dominate the other.

The present spine board 10 provides both great rigidity and light weight—the spine board weighs approximately 11–16 pounds. This is accomplished via a system of reinforcing tubes 50 that impart rigidity to the shell 12 of the spine board 10 via a link provided by the speed pins 40. The interlocking nature of these elements is established both through their particular design and by the manner in which the board is manufactured, which shall now be discussed.

Briefly, the skeletal elements of the spine board are first assembled and placed within the cavity of a rotational mold. The skeletal elements comprise the graphite tubes 50 and the speed pins 40. The outer shell 12 is then rotationally molded about the skeletal elements, causing the outer shell 12 to surround and encase the interior elements. The interior spaces are then filled with a semi-rigid foam 30.

Two pultruded graphite tubes 50, made of a unidirectional vinyl ester/carbon fiber material, are employed as the primary skeletal stiffening elements. While other materials can be used for the stiffening elements (e.g., glass reinforced plastics, phenolic and fabric composites, epoxy glass reinforced materials etc.), the use of graphite tubes is preferred as this material and shape provides great rigidity with little penalty for weight.

The tubes 50 are each connected to a series of speed pins 40 (see FIGS. 8 and 9). These speed pins 40 are made of a material which is sufficiently thermally stable that it can make contact with the hot mold surfaces of a rotational mold without deteriorating, melting or breaking down. In general, the material employed must be able to withstand temperatures in excess of 400 degrees Fahrenheit. They must also offer a high degree of mechanical integrity in use when subjected to the kinds of stresses which the securement of a patient to the spine board will likely impose on them, and be cost-effective. Materials suitable for this purpose include vinylester with carbon fiber strands, polyphenylene sulfide, polysulfone, polyester, polyetherimide, polyetheretherketone, phenolic, urea formaldehyde, melamine, various thermosetting injection moldable plastics, cast and machine aluminum, monel, and other metals. Additionally, wire forms, pressure stamped sheet metal materials and investment castings can be employed, although a polymer such as vinyl ester carbon fiber is preferred due to its superior strength to weight ratio.

In the illustrated embodiment, six speed pins 40 are connected to each tube 50, although a fewer or greater number of speed pins 40 can be used. The number and location of the speed pins 40 employed is driven by two considerations. First, in the finished board 10, their exposed central portions 41 (the only portion visible as it projects through the wall of the rotationally molded outer shell 12) provide locations along which straps can be attached via quick-action clips—hence the term "speed pin". (Alternatively, the clip portion of the speed pin can be a complete ring of material that is then slid onto the reinforcing tube.) Second, the speed pins 40 also serve as locational elements during the formation of the outer shell 12, during which they hold the reinforcing tubes 50 in place within the cavity of the rotational mold prior to and during molding. Thereafter they continue to provide a measure of mechanical linkage between the tubes 50 and the outer shell 12.

The speed pins 40 are snap-fitted to the reinforcing tubes 50 via curved, snap-on portions 42 located at the medial ends of the speed pins 40 (see FIGS. 8 and 9). At their lateral extremities 46, the speed pins 40 terminate with a locating tab 44A which, in conjunction with the locating tab 44B on the medial end of the speed pin, enable the mold operator to locate and fix the speed pins 40 in space within the rotational molding tool employed. Hence, the initial step in the manufacture of the spine board calls for establishing a framework of speed pins 40 and reinforcing tubes 50 that are held in place within a rotational mold prior to the introduction of any molding material. By insert molding the reinforcing tubes 50 and speed pins 40 in place, they can be positioned very close to where the outer shell 12 is formed, in the region between the hand holes 22 and the pediatric holes 24 (see FIGS. 4–7, which further illustrate the location of the reinforcement tubes 50).

Providing such close proximity of the tubes 50 to the outer shell 12 offers several advantages over prior approaches. First, it facilitates the formation of webbing of the material of the shell onto the reinforcing tubes 50 during the rotational molding of the shell. Such connections serve to further link the tubes with the shell. (This aspect of the invention is utilized in the embodiment discussed further below with respect to FIG. 10.) Second, by locating the reinforcing tubes 50 near the lateral periphery of the board, they leave the central portion of the board clear of stiffening elements that could interfere with the x-ray visualization the patient.

Once the speed pins 40 and reinforcing tubes 50 are in place within the mold, the mold is rotated and filled with a quantity of molten polymer, such as high density polyethylene. The rotation of the mold tool causes the molten polymer to flow to the inner walls of the mold, thereby forming the rotationally molded shell 12. This process is approximately twenty minutes in length.

The rotational mold will reach temperatures of up to 500 Degrees Fahrenheit. However, the most uniform ambient temperature will likely be in the region of 350 to 400 Degrees Fahrenheit. The graphite tubes 50 are held in place using plastic molded components, i.e., the speed pins 40 (now serving as localization devices) positioned along the length of the reinforcing tubes 50. The reinforcing tubes 50 do not make direct contact with the surface of the rotational mold at any time during this process. During this process the molten material of the shell adheres to the outer (lateral) ends of the speed pins, providing both a firm mechanical connection and a hermetic seal of the shell 12 against the speed pins.

The thickness of the shell varies, from a maximum thickness of 0.15 inches in the regions of the handles (where stresses are apt to be highest), to 0.09 inches elsewhere. Further control over the thickness of any part of the shell can be exercised by varying the temperature of the facing portion of the mold (the material tends to build up most effectively when the temperature is greatest).

As is conventional in molding processes, the outer shell 12 is formed with limited number of entry and venting ports 60. These ports are used for the purpose of filling the product with stiffening foam 30, and for venting air or other gases from the product when the foam is introduced into the system.

Once the shell is formed, both it and its internal framework are removed from the rotational mold and permitted to cool, during which time the material of the shell contracts some so as to form a hermetic seal against the speed pins. At this point, the reinforcement tubes 50 are connected to the outer shell by the speed pins 40. This mechanical link can be augmented with webbing between inside wall of the outer shell 12 and the reinforcement tubes 50.

In standard rotational molding procedures, care must be taken that facing interior walls not be too close to one another, lest the material of the walls "web" across the gap during the molding process. This can be used to positive effect in the manufacture of the spine board 10, as is illustrated in the embodiment shown in FIG. 10. Here, selected portions of the reinforcing elements 50 are further bound to the shell 12 via a web of material that extends from facing parts of the outer shell to encircle and bound the reinforcing elements 50. In effect, the webbing acts as a connector element, linking the reinforcing elements to the outer shell 12. The degree to which this occurs is dependent upon the spacing between these elements, and further varies along the longitudinal extent of the reinforcing tubes 50, being complete in the cross-section shown in FIG. 10, but less complete at other locations (so as to permit the subsequent flow of filler 30 into the periphery of the spine board 10). This connection further integrates the reinforcing elements and spine board shell together into a mechanically unitary structure.

Once the rotationally molded outer shell 12 has been formed, it is filled with a quantity of liquid foam, which imparts additional strength and rigidity to the spine board as it solidifies. One foam which may be employed is catalyzed urethane foam. A number of filling processes may be employed, including reaction injection molding (RIM), in which a single or multi-component chemical system is injected in such a manner as to utilize the rotationally molded component of the spine board as a mold in its own right.

The foam 30 is injected into the shell 12 by means of the entry ports 60 located in the back of the spine board (see FIG. 1B). (Alternatively or additionally, the reinforcing tubes 50 may be provided with holes so that they can be used as conduits to channel the catalyzed urethane foam to the extremities of the spine board 10.) In this manner, the rotationally molded component of the spine board outer shell 12 is utilized as a mold for receiving the urethane foam 30. During this operation the spine board is held in form-following wooden jigs to prevent the spine board from distorting under the injection and expansion pressures of the urethane foam.

Once the foam has set, the spine board is released from the jigs. At this stage circular injection molded closures, in the form of caps, are placed into the filling and venting ports on the back of the spine board. These circular caps are "Spin-Welded" into position in the conventional manner in order to hermetically seal off the interior of the spine board from its exterior. Such sealing greatly reduces the likelihood that the interior of the board will become a source of infection, and also simplifies the steps that must be taken to clean and disinfect the board between uses.

A further prophylaxis against bacteria and other microbes can be provided by the material of the board itself. A time-release antimicrobial additive may be placed within the material of the spine board. In general terms, the additive must be sufficiently stable so as to withstand the thermal stresses presented by the rotational molding process without significant reduction in efficacy, and must be suitable for contact with a patient's skin. Such additives are commercially available, as for example, an additive manufactured by Microban Products Company, of Huntersville, N.C. that is sold under the trade name Microban®. The additive can be compounded into the raw molding materials employed for the speed pins 40, outer shell 12, or strapping. The antimicrobial additive resides, after molding of the plastic material, within the interstitial spaces of the polymer. The apparent relatively high vapor pressure of some anti-microbial additives causes the additive to release slowly over time. Therefore, the spine board has "Antimicrobial Time Release" properties, providing an additional measure of protection against bacteria.

It is often desirable to provide molded-in graphics in a spine board, often using block lettering. However, such block lettering may be incompatible with the use of an antimicrobial agent in the shell, as it may present a region where the agent is ineffective. This problem can be avoided by using a molded-in graphic system utilizing specially designed "outline lettering". Such lettering is selected to be of a thickness and type and style suitable to allow reliance on the efficacy of an "Antimicrobial Zone of Inhibition", as this is defined by the Kirby-Bauer Test Methodology. Provided that no point contained within the two dimensional graphic symbols used is further away from the outer boundary of the graphic symbology than twice the effective "Zone of Inhibition" of the Antimicrobial Spine board, the agent will still be effective in use. This ensures that bacteria are kept to a minimum across the whole Spine board, and that there are no regions of the graphics which lack effective antimicrobial activity.

Thus, the present invention provides a hygienic, light weight spine board that remains rigid through many uses.

What is claimed is:

1. A spine board comprising:
    an outer shell;
    at least one stiffening element located within a space defined by the outer shell;
    at least one connector linking the stiffening member to the outer shell; and
    a filler between the stiffening member and the outer shell.

2. A spine board as set forth in claim 1, wherein the stiffening elements are elongated rods.

3. A spine board as set forth in claim 1, wherein the stiffening elements are tubes.

4. A spine board as set forth in claim 3, wherein there are two stiffening elements.

5. A spine board as set forth in claim 4, wherein the stiffening elements comprise graphite.

6. A spine board as set forth in claim 5, wherein the stiffening elements are pultruded.

7. A spine board as set forth in claim 5, wherein the stiffening elements comprise a vinyl ester-carbon fiber material.

8. A spine board as set forth in claim 1, wherein there are two stiffening elements and a plurality of connectors linking each of the stiffening elements with the outer shell.

9. A spine board as set forth in claim 8, wherein the outer shell is made of a polymer.

10. A spine board as set forth in claim 9, where the outer shell is made of high density polyethylene.

11. A spine board as set forth in claim 9, wherein the outer shell forms a hermetic seal with the connectors.

12. A spine board as set forth in claim 9, further comprising handles along the periphery of the board.

13. A spine board as set forth in claim 9, further comprising a series of webs of material extending from the shell to the stiffening elements.

14. A spine board as set forth in claim 13, further comprising a plurality of pediatric holes for facilitating the securement of children to the spine board with strapping.

15. A spine board as set forth in claim 13, further comprising:
a plurality of hand holes along the periphery of the spine board; and
a plurality of pediatric holes inwardly located from the hand holes for facilitating the securement of children to the spine board;
wherein the stiffening elements are positioned within the outer shell between the hand holes and the pediatric holes.

16. A spine board as set forth in claim 9, wherein the proximity of the connectors and stiffening elements to the outer shell is such as to encourage the formation of webbing from the inside surface of the outer shell to the connectors and the stiffening elements.

17. A spine board comprising:
an outer shell;
at least one stiffening element located within the space defined by the outer shell;
at least one connector linking the stiffening member to the outer shell, the connector having two ends, one of which is attached to the stiffening element and the other of which is connected directly to the outer shell; and
a filler between the stiffening member and the outer shell.

18. A spine board comprising:
an outer polymer shell that contains an antimicrobial material that is integral with the shell;
two stiffening element located within the space defined by the outer shell;
a plurality of connectors linking each stiffening member to the outer shell; and
a filler between the stiffening members and the outer shell.

19. A spine board comprising:
a polymeric outer shell defining an interior space and having an upper surface, a lower surface, and a peripheral surface linking the upper surface to the lower surface, said outer shell having a length and a width;
at least two stiffening members located within the outer shell, said stiffening members extending approximately the length of the outer shell of the spine board; and
connectors linking the stiffening members to the outer shell.

20. A spine board as set forth in claim 19, further comprising a series of webs of material extending from the shell to the stiffening members.

21. A spine board as set forth in claim 19, wherein the proximity of the connectors and stiffening members to the outer shell is such that it encourages the formation of webbing from the inside surface of the outer shell to the stiffening members and connectors.

22. A spine board as set forth in claim 19, wherein the stiffening elements comprise granite.

23. A spine board as set forth in claim 22, wherein the stiffening elements are tubular.

24. A spine board as set forth in claim 19, wherein the stiffening elements are located near the periphery of the spine board.

25. A spine board as set forth in claim 19, wherein the spine board comprises a series of handles located along the periphery of the spine board.

26. A spine board as set forth in claim 25, wherein the handles each comprise a hole that passes through the spine board.

27. A spine board as set forth in claim 19, wherein the periphery of the spine board is curvilinear.

28. A spine board as set forth in claim 19, wherein the lower surface of the spine board has a plurality of protrusions for serving as ground contact locations.

29. A spine board as set forth in claim 19, further comprising wear skids.

30. A spine board as set forth in claim 29, wherein the wear skids are detachable from the spine board.

31. A spine board as set forth in claim 29, wherein the end of the connectors that is connected to the stiffening element clips onto the stiffening element.

32. A spine board set forth in claim 29, wherein the connectors are configured so that they can be slid onto the stiffening elements.

33. A spine board as set forth in claim 29, wherein the spine board has a plurality of holes near the periphery of the spine board, and the connectors project through the walls of the outer shell at these holes, thereby exposing the central pin-like portion of the connectors.

34. A spine board as set forth in claim 19, wherein the connectors are made of a material that can maintain its mechanical integrity after being heated to 400° F.

35. A spine board as set forth in claim 34, wherein the material of the outer shell seals against the connectors where they penetrate the outer shell of the spine board.

36. A spine board as set forth in claim 17, wherein the connectors are made of plastic.

37. A spine board comprising:
a polymeric outer shell defining an interior space and having an upper surface, a lower surface, and a peripheral surface linking the upper surface to the lower surface, said outer shell having a length and a width and containing an antimicrobial material that is an integral part of the outer shell;
at least two stiffening members located within the outer shell, said stiffening members extending approximately the length of the outer shell of the spine board; and
connectors linking the stiffening members to the outer shell.

38. A spine board comprising:
a polymeric outer shell defining an interior space and having an upper surface, a lower surface, and a peripheral surface linking the upper surface to the lower surface, said outer shell having a length and a width;
at least two stiffening members located within the outer shell, said stiffening members extending approximately the length of the outer shell of the spine board;

a series of webs of material extending from the shell to the stiffening members; and connectors linking the stiffening members to the outer shell, wherein the connectors have first and second end portions and a central, pin-like portion.

39. A spine board comprising:

a polymeric outer shell defining an interior space and having an upper surface, a lower surface, and a peripheral surface linking the upper surface to the lower surface, said outer shell having a length and a width, and said lower surface having a plurality of protrusions for serving as ground contact locations;

at least two stiffening members located within the outer shell, said stiffening members extending approximately the length of the outer shell of the spine board; and connectors linking the stiffening members to the outer shell, the connectors having two end portions, wherein one of the end portions of the connectors is imbedded within the material of the outer shell and the other of the end portions of the connectors is directly connected to one of the stiffening elements.

40. A spine board as set forth in claim 39, further comprising locating tabs for facilitating the location of the connectors within a mold.

41. A spine board as set forth in claim 39, wherein the spine board is manufactured by rotationally molding the outer shell about the connectors and stiffness members so as to bring about the bridging of liquefied material from the inside surface of the outer shell to the connectors and the stiffening elements.

42. A spine board comprising:

a polymeric outer shell defining an interior space and having an upper surface, a lower surface, and a peripheral surface linking the upper surface to the lower surface, said outer shell having a length and a width;

at least two stiffening members located within the outer shell, said stiffening members extending approximately the length of the outer shell of the spine board; and connectors linking the stiffening members to the outer shell, the connectors being made of a material that can maintain its mechanical integrity after being heated to 400 degrees F., and the connectors have central pin-like portions that are configured to receive the attachment hardware of a strap.

43. A spine board comprising:

a polymeric outer shell defining an interior space and having an upper surface, a lower surface, and a peripheral surface linking the upper surface to the lower surface, said outer shell having a length and a width;

at least two stiffening members located within the outer shell, said stiffening members extending approximately the length of the outer shell of the spine board;

foam between the outer shell and the stiffening members; and connectors linking the stiffening members to the outer shell.

44. A spine board as set forth in claim 43, wherein the foam is of the urethane type.

45. A spine board as set forth in claim 44, wherein the foam is catalyzed urethane foam.

46. A method for manufacturing a spine board, comprising the steps of:

affixing a plurality of speed localization elements having two ends to two carbon graphite reinforcing tubes;

mounting the free ends of the localization elements to the inner wall of a rotational mold;

closing the mold;

charging the rotational mold cavity with a quantity of liquid polymer; and rotating the mold so as to form the outer shell of the spine board.

47. The method of claim 46, wherein during the step of forming the outer shell, liquefied polymer bridges form that link the inner wall of the mold to the reinforcing tubes, thereby further connecting the reinforcing tubes to the outer shell.

48. The method of claim 46, further comprising the steps of:

removing the outer shell from the mold; and charging the cavity within the outer shell with foam.

49. The method of claim 46, wherein the polymer material from which the outer shell is formed contains an antimicrobial additive.

50. A spine board comprising:

a polymeric outer shell defining an interior space and having an upper surface, a lower surface, and a curvilinear peripheral surface linking the upper surface to the lower surface, said curvilinear peripheral surface facilitating the use self-tightening strapping systems with the spine board; and speed pins for facilitating the attachment of strapping to the spine board, said speed pins being hermetically sealed along selected portions with the respect to the shell.

51. A spine board comprising:

a polymeric outer shell defining an interior space and having an upper surface, a lower surface, and a curvilinear peripheral surface linking the upper surface to the lower surface, said curvilinear peripheral surface facilitating the use self-tightening strapping systems with the spine board; and speed pins for facilitating the attachment of strapping to the spine board, said speed pins being hermetically sealed along selected portions with the respect to the shell;

wherein the spine board further comprises a quantity of antimicrobial additive in the outer shell, said antimicrobial additive in the spine board having a zone of inhibition.

52. A spine board as set forth in claim 51, further comprising graphics on the outer shell in the form of outline graphics, the thickness of the outline of such graphics being such that no point contained within the graphics is further away from the outer boundary of the graphic than twice the effective zone of inhibition of the antimicrobial additive in the spine board.

53. A spine board comprising:

an outer shell;

at least one stiffening element located within the space defined by the outer shell; and at least one connector linking the stiffening member to the outer shell, the connector having two ends, one of which is attached to the stiffening element and the other of which is connected directly to the outer shell.

54. A spine board comprising:

a polymeric outer shell defining an interior space and having an upper surface, a lower surface, and a peripheral surface linking the upper surface to the lower surface, said outer shell having a length and a width;

at least one stiffening member located within the outer shell, said at least one stiffening member extending approximately the length of the outer shell of the spine board;

a series of webs of material extending from the shell to the at least one stiffening member; and connectors linking the at least one stiffening member to the outer shell, wherein the connectors have first and second end portions and a central, pin-like portion.

55. A spine board comprising:

a polymeric outer shell defining an interior space and having an upper surface, a lower surface, and a peripheral surface linking the upper surface to the lower surface, said outer shell having a length and a width;

at least one stiffening member located within the outer shell, said at least one stiffening member extending approximately the length of the outer shell of the spine board; and connectors linking the at least one stiffening member to the outer shell, the connectors being made of a material that can maintain its mechanical integrity after being heated to 400 degrees F., and the connectors have central pin-like portions that are configured to receive the attachment hardware of a strap.

56. A method for manufacturing a spine board, comprising the steps of:

affixing a plurality of speed pins having two ends to two reinforcing tubes;

mounting the free ends of the localization elements to the inner wall of a rotational mold;

closing the mold;

charging the rotational mold cavity with a quantity of liquid polymer; and rotating the mold so as to form the outer shell of the spine board.

57. The method of claim 56, wherein during the step of forming the outer shell, liquefied polymer bridges form, linking the inner wall of the mold to the reinforcing tubes, thereby further connecting the reinforcing tubes to the outer shell.

58. The method of claim 56, further comprising the steps of:

removing the outer shell from the mold; and charging the cavity within the outer shell with foam.

59. The method of claim 56, wherein the polymer material from which the outer shell is formed contains an antimicrobial additive.

60. A method for manufacturing a spine board, comprising the steps of:

affixing a plurality of speed pins having two ends to two reinforcing tubes;

mounting the free ends of the localization elements to the inner wall of a rotational mold;

closing the mold;

charging the mold cavity with a quantity of liquid polymer; and subjecting the mold to suitable process conditions so as to form the outer shell of the spine board.

* * * * *